United States Patent [19]

Lisenbee

[11] Patent Number: 4,772,453
[45] Date of Patent: Sep. 20, 1988

[54] LUMINISCENCE MEASUREMENT ARRANGEMENT

[76] Inventor: Wayne F. Lisenbee, 5103 Lillian St., Torrance, Calif. 90501

[21] Appl. No.: 707,496

[22] Filed: Mar. 1, 1985

[51] Int. Cl.$^4$ .................................................. G01N 21/63
[52] U.S. Cl. ......................................... 422/52; 422/73; 436/172; 436/809
[58] Field of Search ................. 422/52, 58, 63, 104, 422/102, 65, 73; 436/47, 165, 172, 809; 269/63, 71; 435/291, 808; 414/749, 750

[56] References Cited

U.S. PATENT DOCUMENTS

| | | | |
|---|---|---|---|
| 3,756,920 | 9/1973 | Kelbaugh et al. | 435/808 |
| 4,022,529 | 5/1977 | White | 250/458.1 |
| 4,055,470 | 10/1976 | Sheaff et al. | 435/808 |
| 4,099,920 | 7/1978 | Heiss | 422/52 |
| 4,142,458 | 3/1979 | Duym | 422/104 |
| 4,234,540 | 11/1980 | Ginsberg et al. | 422/64 |
| 4,276,258 | 6/1981 | Ginsberg et al. | 422/64 |
| 4,314,026 | 2/1982 | Descamps-Latscha | 422/52 |
| 4,396,579 | 8/1983 | Schroeder et al. | 435/291 |
| 4,530,637 | 6/1985 | Mason et al. | 414/750 |
| 4,557,154 | 12/1985 | Iwata et al. | 422/65 |

Primary Examiner—Michael S. Marcus
Attorney, Agent, or Firm—Don B. Finkelstein

[57] ABSTRACT

A high speed, luminescence detection arrangement for sequentially measuring the luminescence emitted from a plurality of luminescence sources under test. A tray holder contains a plurality of cup-like sample wells, from which the luminescent radiation is emitted, and each of the cup-like sample wells is sequentially positioned in a predetermined location to allow the detection and measurement of the intensity of the luminescence emitted therefrom. Display means are provided to provide a detectible display, having a magnitude proportional to the intensity of the luminescence detected. Fluid dispensing means are operatively interconnected to allow injection of one or more fluids into each of the cup-like sample wells at a predetermined time before measurement of the luminescence emitted therefrom.

26 Claims, 7 Drawing Sheets

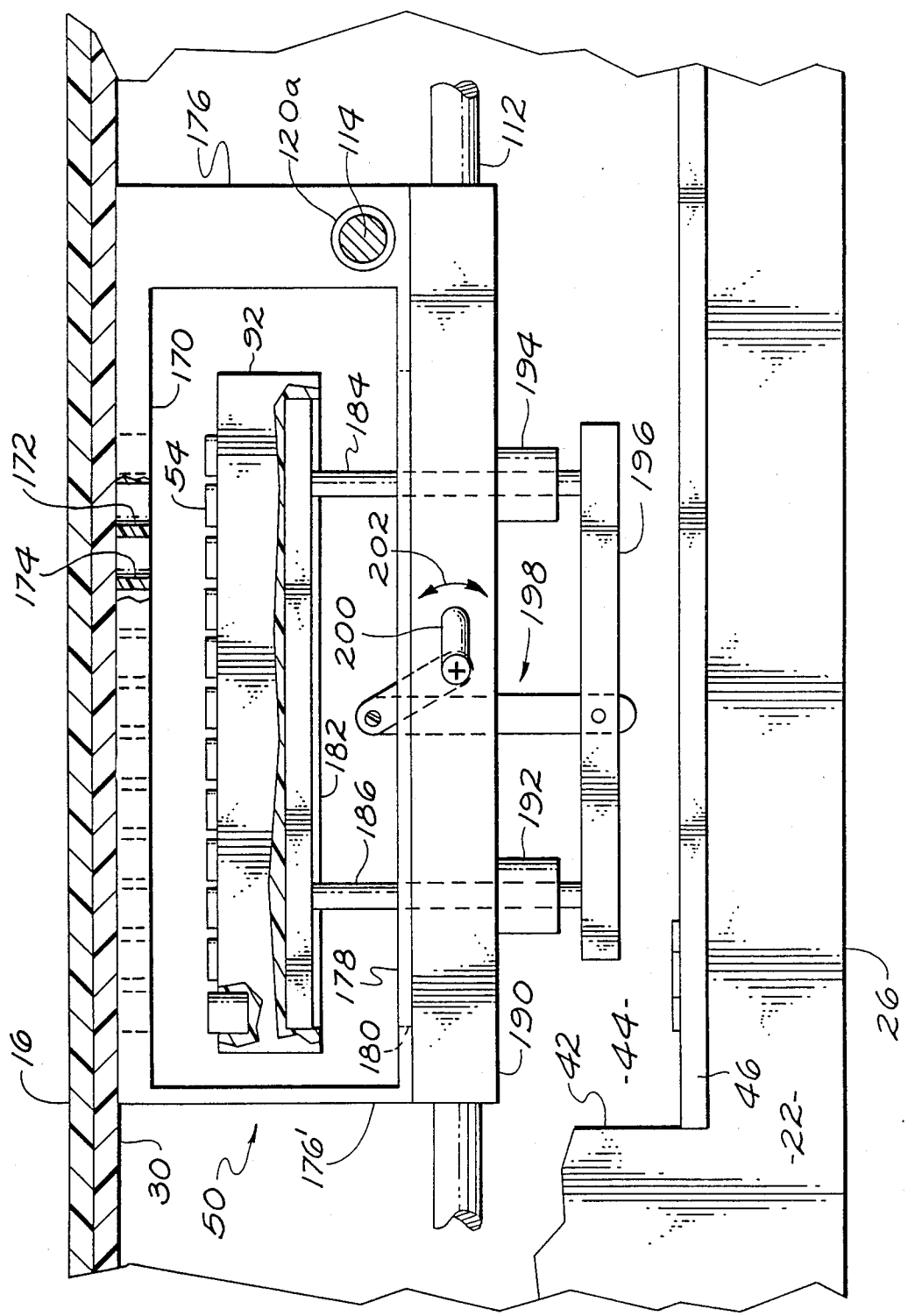

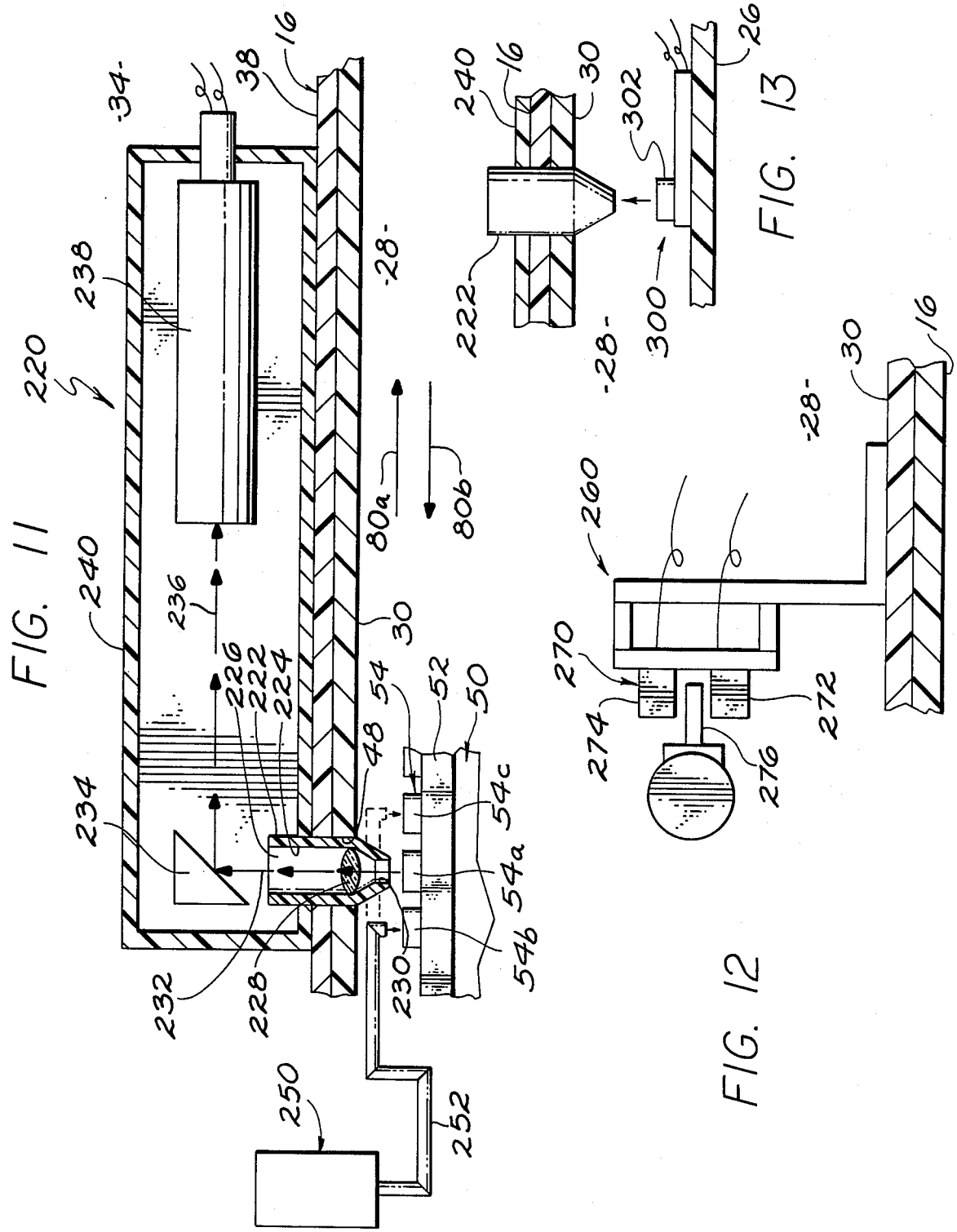

LUMINISCENCE MEASUREMENT ARRANGEMENT

BACKGROUND OF THE INVENTION

1. Field of the Invention

This invention relates to the luminesence detection and measurement art, and, more particularly, to a high speed luminescence detection arrangement for sequentially measuring the luminescence from a plurality of luminescence emitting samples.

2. Description of the Prior Art

As a method of precise analysis in both clinical and research laboratories, Luminescence Immunoassay (LIA) offers extraordinary potential. LIA combines the specificity of immunoassay and the sensitivity of luminescent light detection. Moreover, applications are almost limitless in that all that is needed is a procedure to link a luminescence reactant, such as isoluminol or peroxidase, to the analyte or its antibody availability of antibody to the analyte; and an instrument to measure the luminescent light emitted.

Both bioluminescent (BL) and chemiluminescent (CL) reactions can be utilized in these assays. Bioluminescent reactions are enzymatically mediated by bacterial or firefly luciferase, and involve oxidation of a substrate (usually luciferin) to form products which include light. Luciferase-bound analytes or ATP can be quantitated by correlating the amount of light produced to concentrations of standards. Detection limits of $10^{-16}$ mol ATP, $10^{-18}$ mol TNT, and $10^{-17}$ mol DNP are reported.

Chemiluminescent reactions involve a similar light production, commonly by oxidation of a phthalhydrazide derivative, such as luminol, in the presence of hydrogen peroxide and peroxidase. With naphthalhydrazide and phthalhydrazide derivatives as chemiluminescent labels, detection limits in the range of $10^{-16}$ mol are reported. Analytes include digoxin, thyroxine, IgG, cortisol, insulin, progesterone, and alpha-fetoprotein.

While there have been many procedures offering the specificity inherent to antibody binding, until the development of LIA, radioactive labelling (RIA) was the method of choice due to its sensitivity. LIA has all of the advantages of RIA, including comparable or better sensitivity. In addition, it features low reagent volumes (hence low cost), and nontoxic, stable reagents. Luminescence reagents offer a shelf life of about 2 years as compared with $^{125}$I, a common RIA label, which has an effective shelf life of about thirty (30) days.

The clinical chemist is involved in measuring a variety of substances by many different analytical techniques. Although different, these techniques share the common principle of an interface between chemistry and physics. The most commonly used such interface in clinical chemistry is absorptiometry, both at visible and ultraviolet wavelengths, but emission flame photometry and radioactivity are also commonly used.

Analyses based on the measurement of emitted light, such as luminescent light, offer several advantages over conventional techniques: high sensitivity, wide linear range. low cost per test, and relatively simple and inexpensive equipment.

Luminescence detection has application in several areas of clinical analysis. It has a role as a replacement for conventional colormetric or spectrophotometric indicator reactions in assays for substrates of oxidases and dehydrogenases. In this type of assay the sensitivity of the luminescence indicator reaction may be used either to quantitate substrates not easily measured by conventional techniques (e.g., prostaglandins and vitamins) or to reduce the quantities of specimen and reagent required in the initial enzymatic step, thus reducing the cost of the assay. Another application of luminescence is the utilization of luminescent molecules as replacements for radioactive labels in immunoassay, as noted above.

An important feature of the luminescence as an analytical technique is that its usefulness is not confined to clinical chemistry. Further, luminescence detection has applications in roles in other pathology disciplines, e.g., hematology, immunology, bacteriology, and pharmacology.

Chemiluminescence may be simply defined as the chemical production of light. In the literature it is often confused with fluorescence. The difference between these two processes is the source of energy that is producing molecules in an excited state. In chemiluminescence, this is the energy of a chemical reaction, and the decay from the excited state back to the ground state is accompanied by emission of light (luminescence). In contrast, incident radiation is the source of the energy that, in fluorescence, promotes molecules to an excited state. Analytically, the types of luminescence that have engendered the most interest are chemiluminescence and bioluminescence. The latter is the name given to a special form of chemiluminescence found in biological systems, in which a catalytic protein increases the efficiency of the luminescent reaction. Indeed, in certain cases the reaction is impossible without a protein component.

Of the several advantages of luminescent methods over their conventional counterparts, their extreme sensitivity is the most important. For example, as compared with spectrophotometry, the BL assay of NADH is estimated to be some 25,000-fold more sensitive, and BL assays for glucose and alcohol are, respectively, 55- and 10-fold more sensitive than conventional assays. The minimal detectable concentration for an assay ultimately depends on how sensitively light can be detected, and on the quantum efficiency of the reaction. Generally BL reactions are much more efficient than CL reactions; typical quantum efficiencies are in the ranges 0.1–0-8 and 0.01–0.05, respectively.

Since CL is an emission process (as opposed to absorption), response is usually linearly proportional to concentration from the minimal detectable concentration up to the point where it is no longer possible to maintain an excess of other reactants relative to the analyte. In the case of ATP assay by the firefly reaction, response is linear over six orders of magnitude.

The speed of analysis largely depends on the type of luminescent reaction. In some instances a rapid flash is obtained (1 s), the peak height of which may be related to analyte concentration; in other cases a more protracted glow occurs when a time course lasting several minutes. In the latter case, the integral or partial integral of the light-time curve has been used as a measure of analyte concentration because it is much less sensitive to mixing efficiency, but this drastically reduces the through-put and speed of analysis.

The major cost benefit of luminescent assays arises from their extreme sensitivity, which allows assays to be performed with much less reagents, hence reducing the cost per test. For example, luminescence offers a means of reducing the cost of cholesterol assays involving cholesterol oxidase (EC 1.1.3.6), because the sensitivity of CL detection of peroxide allows the initial peroxide-producing reaction involving cholesterol oxidase to be scaled down.

Specificity is conferred on BL and CL by using the luminescence as an indicator reaction coupled to intermediates (such as ATP, MADH, and $H_2O_2$) produced enzymatically. Generally, BL reactions are specific because they are enzymic processes, but CL reactions are nonspecific. Luminol, for example, will undergo a CL reaction with various oxidants (oxygen, peroxide, superoxide, iodine) and its reactions are subject to interferences by reducing agents such as uric acid.

In practical applications of the principles of bioluminescence and chemiluminescence as above described, it is necessary to provide a detection and measuring arrangement for detecting and measuring the luminescence emitted from the sample under test. Further, the arrangement should include a display for displaying the signal indicative of the intensity of the luminescence emitted. One prior art device, utilized for such luminescence detection measuring applications, required that each separate sample under test be separately placed into the device. Reagents necessary to achieve luminescence with the sample under test could be added prior to insertion of the sample into the device or after insertion. The luminescence from the one sample was then detected and measured, and a display indicative of the amount of luminescence was provided. The sample was then removed and another sample could then be installed. Such sampling on a one-at-a-time basis was time consuming, and did not lend itself to applications requiring high speed, rapid, determination of the luminescence emitted from a plurality of samples.

Accordingly, there has long been a need for a luminescence detection measuring arrangement in which a plurality of samples under test may be rapidly subject to measurement of the luminescence emitted therefrom and a display, indicative of the intensity of the luminescence from each separate sample under test be provided.

SUMMARY OF THE INVENTION

Accordingly, it is an object of the present invention to provide an improved luminescence detection and measuring arrangement.

It is another object of the present invention to provide an improved luminescence detection and measuring arrangement, which rapidly detects and measures the luminescence emitted from a plurality of samples under test.

It is another object of the present invention to provide an improved luminescence detection arrangement which is comparatively easy to utilize, is comparatively inexpensive, and provides repetitive, accurate, indications of the intensity of the luminescence emitted from a plurality of samples under test.

The above and other objects of the present invention are achieved, according to a preferred embodiment thereof, by providing a case means which has first walls defining a base chamber and second walls defining an upper chamber. The base chamber is separated from the upper chamber by a top wall portion of the first walls, and, preferably, the first walls provide blocking of ambient light from regions external the case means from entering the base chamber during the luminescence testing. Edge walls, defining an aperture, are provided in the top wall portion. A tray holder means is movably mounted in the base chamber, and adjacent the lower surface of the top wall portion. The tray holder means is adapted to receive and hold a tray containing a plurality of cup-like sample wells. The plurality, for example, may be on the order of 96 arranged in a rectilinear matrix array, having eight rows, and twelve columns.

Motion producing means are provided in the case means to move the tray holder means in response to predetermined signals from a load position (which is also the unload position), wherein the tray holder means extends through an aperture in a front wall portion of the first walls to a plurality of internal positions in the base chamber. Door means are provided on the front wall to close the aperture in the front wall for the condition of the tray holder means in the base chamber. In the plurality of internal positions of the tray holder means, each of the cup-like sample wells is sequentially aligned in a predetermined sequence with the aperture in the top wall portion. A dwell time at each internal position is provided by the motion producing means and during the dwell time, the luminescence emitted from the one cup-like sample well in the aligned position with the aperture in the top wall portion, is measured. The motion producing means is sequenced to move the tray holder means a plurality of internal positions in a known sequence and at a predetermined rate. The total of ninety six samples in this embodiment may be measured in, for example, thirty seconds.

A luminescence detection means is in the case means and has a lens means aligned with the aperture in the top wall portion. The luminescence from the samples is transmitted through the lens means and, in this embodiment of the present invention, is directed onto a prism which redirects the luminescence into a photo-multiplier tube. The photo-multiplier tube provides an output signal which is proportional to the intensity of the luminescence.

A display means, which, for example, may be a digitalized printer, receives the output signal after suitable amplifications and signal conditioning, and provides a detectible display, such as a digitalized numerical printed display, wherein the numerical value printed is proportional to the intensity of the luminescence. It will be appreciated, of course, that other forms of display, such as light emitting diode displays, graphic displays, or other displays, may be utilized, as desired, is response to the magnitude of the output signal.

At the completion of the predetermined sequence of internal positions, the tray holder means is moved to the load-unload position, where it extends through the front wall portion so that the tray containing the cup-like sample wells may be removed. The sequence of operations may be repeated by placing another tray into the tray holder means for detection of the luminescence emitted therefrom.

In some embodiments of the present invention, it may also be desirable to provide a fluid dispensing arrangement in connection therewith, for dispensing predetermined fluids into the cup-like sample wells. Such fluids may be of the type which cause the luminescence to occur from the samples contained within the cup-like sample wells. Thus, in such embodiments, it may also be desirable to inject one or more of such fluids into the cup-like sample wells, immediately preceding the time when it is in an internal position aligned with the aperture in the top wall portion. That is, at the time that the preceding cup-like sample well is aligned, the fluids may be injected into the next cup-like sample well. The dwell time during the detection and measurement of the luminescence provides sufficient time for such injection of the fluids.

BRIEF DESCRIPTION OF THE DRAWINGS

The above, and other embodiments of the present invention may be more fully understood from the following detailed description, taken together with the accompanying drawings, wherein similar reference characters refer to similar elements throughout, and in which:

FIG. 10 is a view along the line 10—10 of FIG. 9;

FIG. 11 is a partial sectional view along the line 11—11 of FIG. 5 and partially in schematic form;

FIG. 12 is a partial sectional view along the line 12—12 of FIG. 3;

FIG. 13 is a partial sectional view illustrating the calibration light source useful in the practice of the present invention.

DESCRIPTION OF THE PREFERRED EMBODIMENTS

Figure 1:
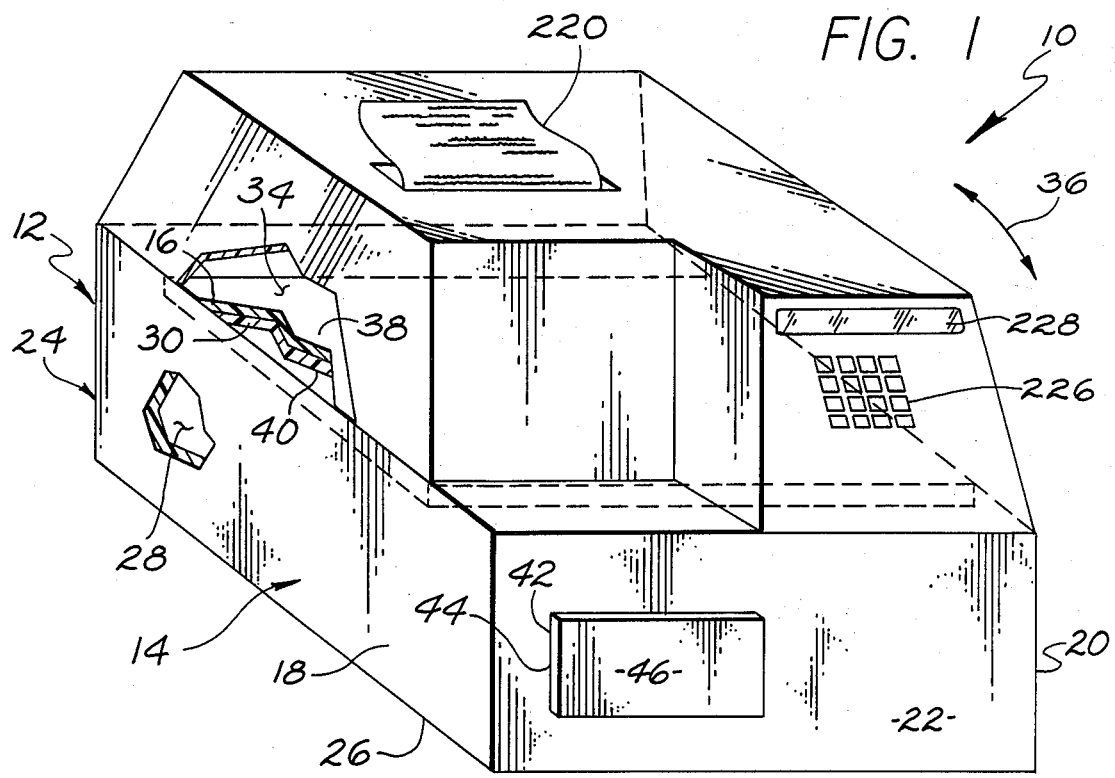
FIG. 1 is a perspective view of one embodiment of the present invention.

Referring now to the drawing, there is illustrated in FIG. 1 a perspective view of a preferred embodiment generally designated 10, according to the principles of the present invention, of an improved luminescence detecting and measuring arrangement. The embodiment 10 has a case means, generally designated 12, having first walls 14, comprising a top wall portion 16, opposed side wall portions 18 and 20, a front wall portion 22, and a back wall portion 24 opposite the front wall portion 22, and a bottom wall portion 26 to define an enclosed box-like base chamber 28, as shown on FIG. 2. For structural support, a mounting plate 30 is coupled to the top wall portion 16. However, the mounting plate 30 does not extend to the front wall 22 as illustrated by the dotted line showing thereof in FIG. 1. In the areas where the mounting plate 30 is coupled to the top wall portion 16, the unitary structure will be referred to hereinafter as the top wall portion 16.

The case means 12 also has second walls 32, defining an upper chamber 34. The second walls 32 are, in the embodiment 10, hingedly mounted on the first walls 14 along the top of the rear wall portion 24, to provide access to the upper chamber 34, and, therefore, are movable in the directions indicated by the double ended arrow 36 from the closed position as indicated in FIG. 1 to an open position. The top wall portion 16 of the first walls 14 has an upper surface 38 in the upper chamber 34, and a lower surface 40 in the base chamber 28.

Figure 2:
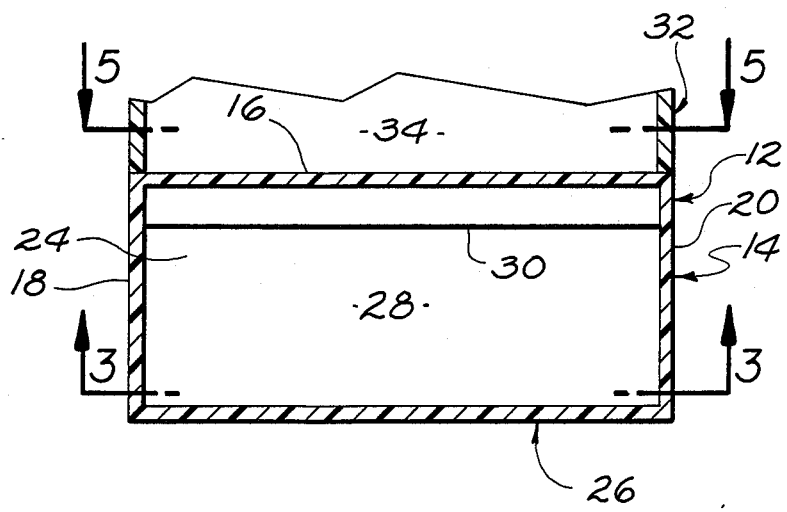
FIG. 2 is a sectional view of the embodiment shown in FIG. 1, with the internal structure removed to show the configuration thereof.

The front wall portion 22 of the first walls 14 has edges 42 defining a tray receiving aperture 44 therethrough, and the tray receiving aperture 44 in the front wall portion 22 is closed by a door means 46, hingedly mounted on the front wall portion 22 along the bottom edge portion 42a. In FIG. 2, the structures contained in the base chamber 28 and the upper chamber 34 has been omitted for clarity in showing the structural arrangement.

Figure 3:
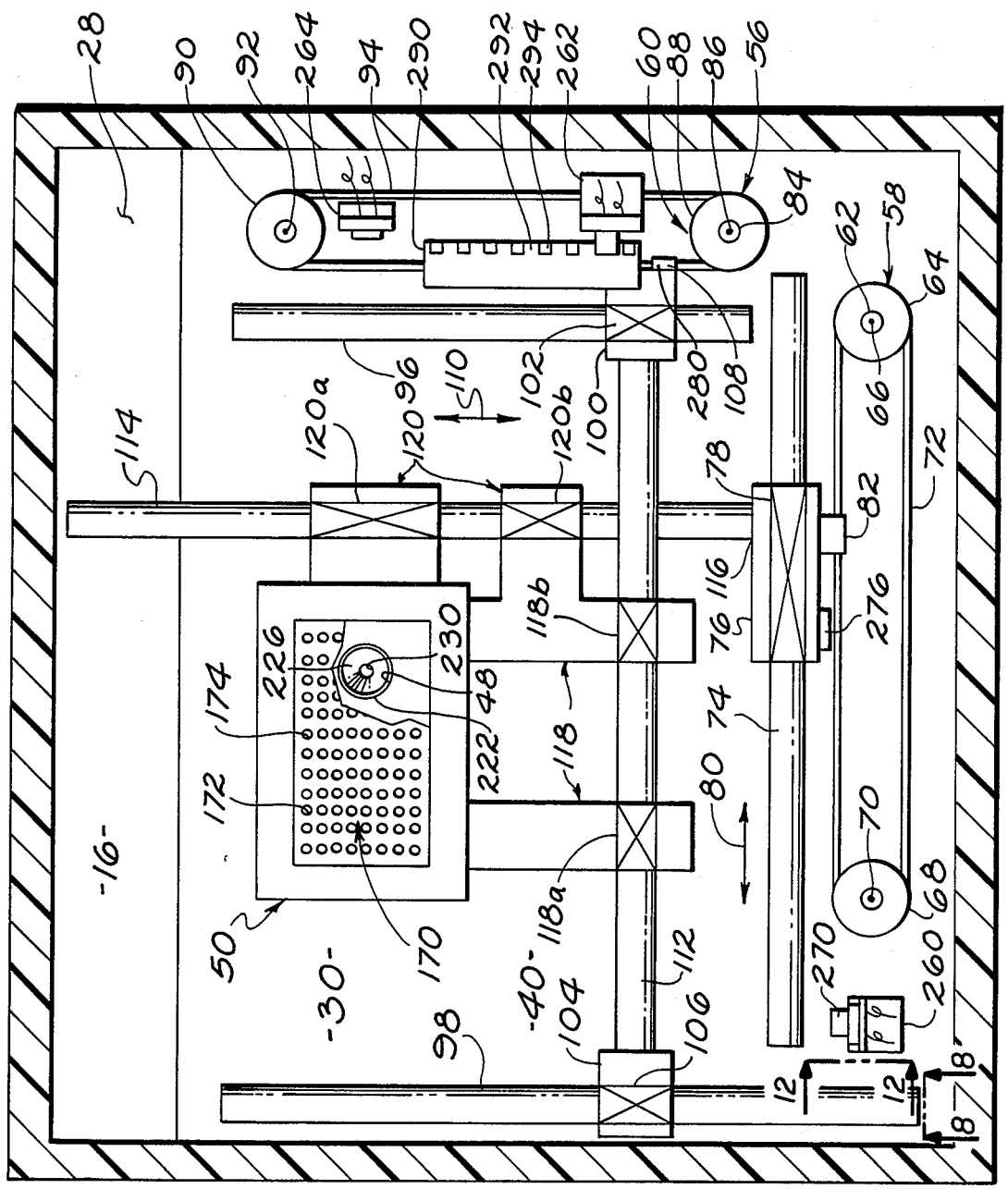
FIG. 3 is a sectional view along the line 3—3 of FIG. 2, showing the structure associated with the motion producing means of the present invention.

FIG. 3 is a sectional view along the line 3—3 of FIG. 2, illustrating structure mounted in the base chamber 28. As shown in FIG. 3, the top wall portion 16 (and mounting plate 30) have edges defining an aperture 48 therethrough. A tray holder means, generally designted 50, is movably mounted in the base chamber 28, and, as described below in greater detail, has a load position in which at least a portion of the tray holder means 16 extends through the tray holder receiving aperture 44 in front wall 22 to allow positioning in the tray holder means 50 of a tray containing a plurality of cup-like sample wells, which contain the material to be tested for luminescence.

Figure 4:
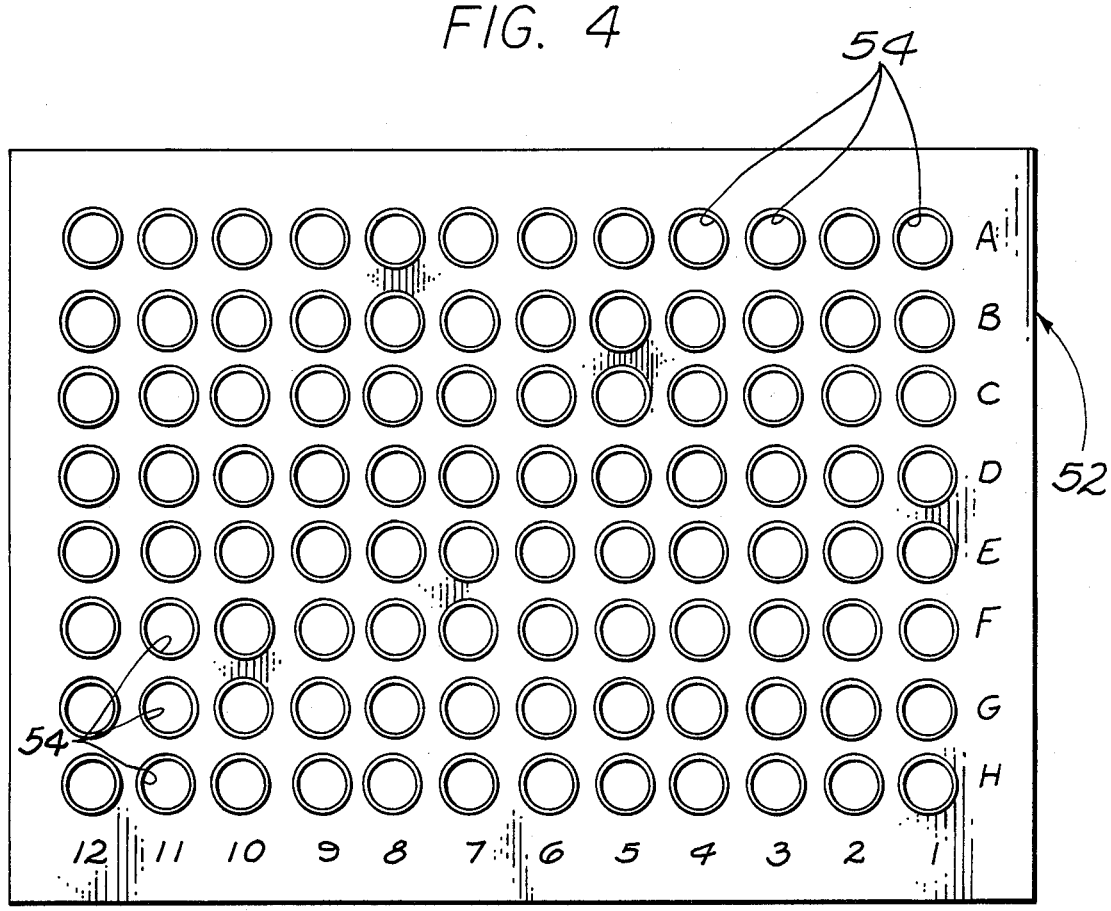
FIG. 4 illustrates a sample tray, containing the plurality of cup-like sample wells utilized in the practice of the present invention.

FIG. 4 illustrates a tray, generally designated 52, having a plurality of cup-like sample wells 54 thereon. As mounted in the tray holder means 50, the open end of the cup-like sample wells 54 face upwardly toward the mounting plate 30. The plurality of cup-like sample wells 54 are arranged in a preselected array, and, as illustrated in FIG. 4, comprise a rectilinear matrix having eight rows and twelve columns, for a total of ninety-six separate cup-like sample wells 54. Each of the cup-like sample wells 54 are sequentially positioned in an aligned relationship with the aperture defined by the edges 48 in the top wall portion 16.

In order to selectively move the tray-holder means, and thus the plurality of cup-like sample means in a predetermined sequence in alignment with the aperture defined by the edges 48, motion producing means, generally designated 56 are provided and mounted on the top wall portion 16. The motion producing means are operatively connected to the tray holder means for selectively moving the tray holder means between the load (and unload) position wherein the tray holder means 50 extends through the tray holder receiving aperture 44 with the door 46 in the open position thereof to a plurality of internal positions within the base chamber. Each of the plurality of internal positions of the tray holder means 50 corresponds to the alignment of one of the cup-like sample wells 54 with the aperture defined by the edges 48.

Referring again to FIG. 3, the tray 52 has been omitted for clarity. The motion producing means 56 provides the movement of the tray holder means 50 in mutually perpendicular directions. To achieve this sequential movement in mutually perpendicular directions, the motion producing means 56 in general comprises first drive means 58 and second drive means 60. The first drive means 58 comprises a drive shaft 62 extending through the top wall portion 16 and rotates a first pulley 64 about a first axis 66. A second pulley 68 is mounted on the top wall portion 16 in spaced relationship to the first pulley 64, for rotation about a second axis 70, which is substantially parallel to the first axis 66. A first belt means 72 extends between the first pulley 64 and the second pulley 68 and is movable therearound for the condition of rotation of the first drive shaft 62.

The first guide rod means 74 is mounted on the lower surface 40 of the top wall portion 16 and is spaced therefrom a predetermined distance. The first guide rod 74 extends substantially parallel to the plane containing the first axis 66 and the second axis 70. A first slide means, generally designated 76 is slidably mounted by, for example, the first slide bearing 78 on the first guide rod 74 for sliding movement therealong in the directions indicated by the double ended arrow 80. The first slide means 76 is coupled to the first belt 72, as indicated at 82. Movement of the first belt means 72 in the directions indicated by the double ended arrow 80 moves the first slide means 76 along the first guide rod means 74. The tray holder means 50, as described below in greater detail, is operatively coupled to the first slide means 76 for movement in the direction indicated by the double ended arrow 80.

The second drive means 60 comprises a second rotatable shaft 84, extending through the top wall portion 16 into the base chamber 28 for rotation about a third axis 86. A third pulley 88 is mounted on the second drive shaft 84 for rotation therewith. A fourth pulley 90 is rotatably mounted in the base chamber 28 in spaced relationship to the third pulley 88 for rotation about a fourth axis 92, which is substantially parallel to the third axis 86. A second belt means 94 extends between the third pulley 88 and the fourth pulley 90 for movement therearound.

A second guide rod means 96 and a third guide rod means 98 are mounted on and spaced from the lower surface 40 of the top wall portion 16 in the base chamber 28 in parallel, aligned, spaced apart relationship, and parallel to the plane containing the third axis 86 and fourth axis 92. A second slide means 100 is slidably mounted on the second guide rod 96 by a second slide bearing 102 which is generally similar to the slide bearing 78. A third slide means 104 is slidably mounted on the third guide rod means 98 by a third slide bearing 106 which may be similar to the slide bearing 78. The second slide means 100 is coupled to the second belt 94 as indicated at 108 for movement therewith between the third pulley 88 and the fourth pulley 90 in directions indicated by the double ended arrow 110, which are mutually perpendicular to the directions indicated by the arrow 80 described above. The tray holder means, as described below, is operatively connected to the second slide means 100 and third slide means 104 for movement therewith in the directions indicated by the double ended arrow 110.

A fourth guide rod means 112 is coupled to the second slide means 100 and third slide means 104, and extends therebetween substantially parallel to the first guide rod means 74. The fourth guide rod means 112 moves in the directions indicated by the arrow 110 with movement of the second and third slide means 100 and 104, respectively. A fifth guide rod means 114 is coupled to the first slide means 76, as indicated at 116, and the fifth guide rod 114 is mounted on the lower surface 40 of the top wall portion 16 in the base chamber 28 and aligned in parallel relationship to the second guide rod means 96 and third guide rod means 98.

Fourth slide means, generally designated 118, is coupled to the tray holder means 50 and slidingly mounted on the fourth guide rod 112 by a pair of spaced apart slide bearing means 118a and 118b. It will be appreciated, of course, that a single slide bearing could be utilized for the fourth slide means 118, if desired. The slide bearings 118a and 118b move on the fourth guide rod means 112 in directions indicated by the arrow 80.

Fifth slide means 120 is coupled to the tray holder means 50 and slidingly mounted on the fifth guide rod means 114 for sliding movement therealong in the directions indicated by the arrow 110 and, in the embodiment 10, the fifth slide means comprises a pair of spaced apart slide bearings 120a and 120b. It will be appreciated, of course, that a single slide bearing could be utilized in place of the two spaced apart slide bearings 120a and 120b.

Rotation of the first drive shaft 62 moves the first belt 72 in the directions indicated by the arrow 80, thereby moving the first slide means 76 in the directions indicated by the arrow 80 and, since the fifth guide rod 114 is coupled to the first slide means 76, the tray holder means 50 is moved in the directions indicated by the first arrow 80. Similarly, rotation of the second drive shaft means 84 moves the second belt means 94 in the directions indicated by the arrow 110, and, because of the connections at 108 to the second slide means 102, moves the tray holder means 50 in the directions indicated by the arrow 110.

The first drive means 58 and second drive means 60 further comprise means for providing the rotation of the first drive shaft 62 and second drive shaft 84. Such rotation producing means may be various types of motors combined with various types of mechanical drives. For example, a stepping motor may be utilized, a Geneva drive may be utilized, or the like.

Figure 5:
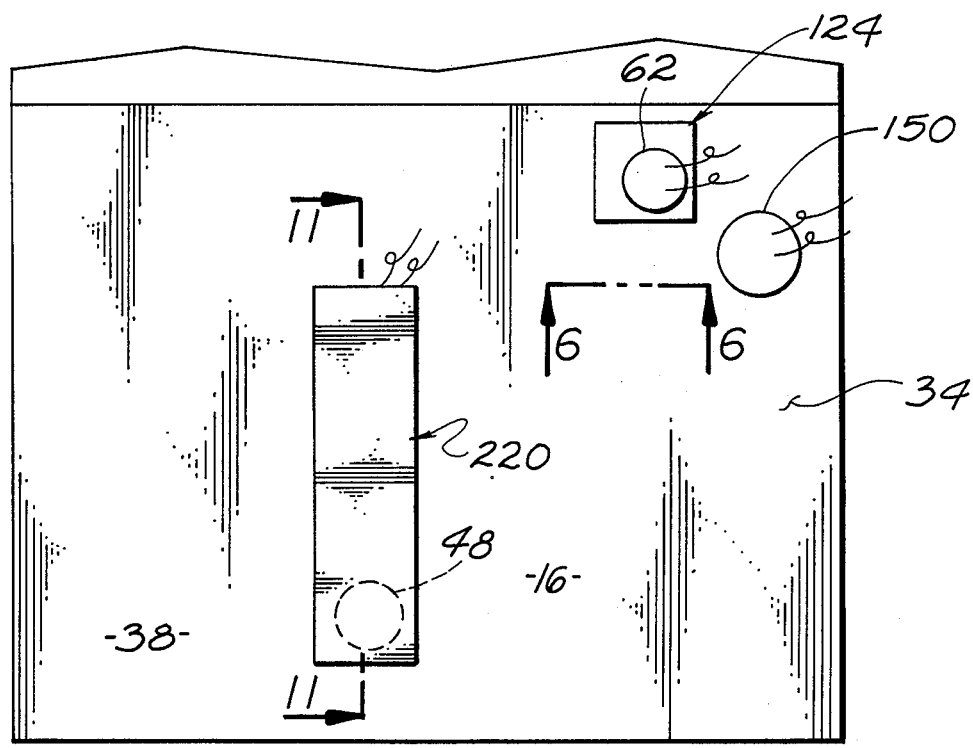
FIG. 5 is a view along the line 5—5 of FIG. 2 showing the structure as appearing therein.
Figure 6:
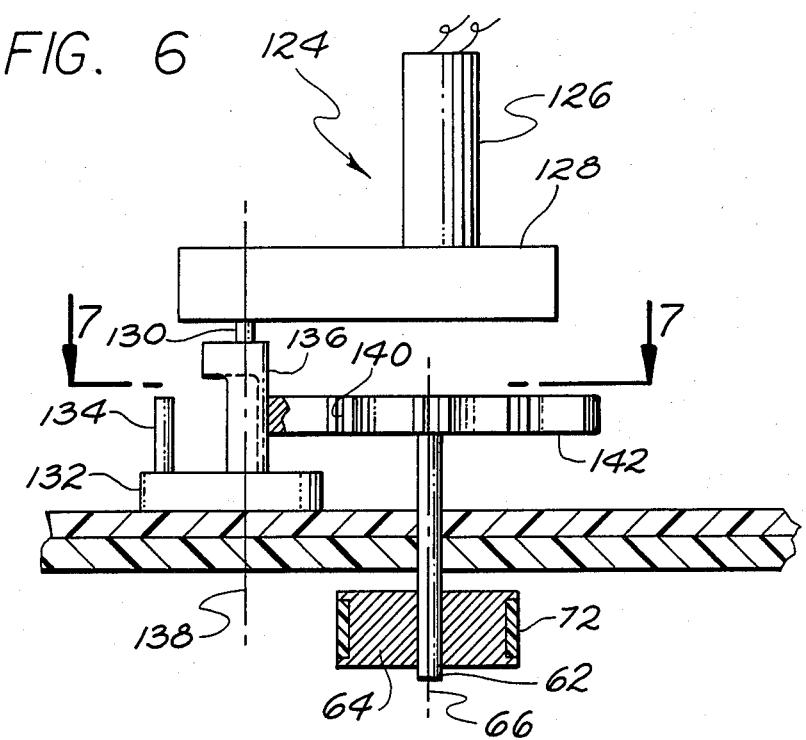
FIG. 6 is a view along the line 6—6 of FIG. 5, illustrating the Geneva drive useful in the practice of the present invention.
Figure 7:
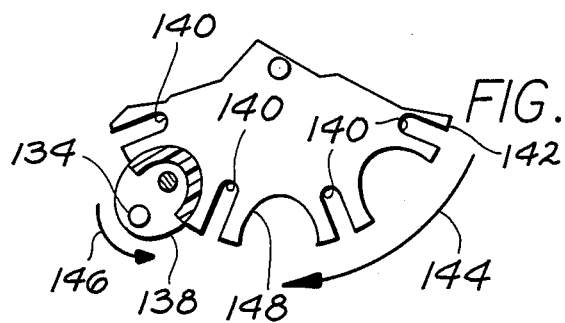
FIG. 7 is a partial sectional view along the line 7—7 of FIG. 6.

FIG. 5 illustrates a view along the line 5—5 of FIG. 2, showing the motion producing means for rotating the first drive shaft and second drive shaft. As illustrated in FIG. 5, the first drive shaft 62 is rotated by a Geneva drive means, generally designated 124. The Geneva drive means 124 is more fully illustrated in FIGS. 6 and 7. FIG. 6 is a view along the line 6—6 of FIG. 5, and FIG. 7 is a view along the line 7—7 of FIG. 6. As shown, the Geneva drive 124 has a motor 126 connected to a gear box 128 which drives a cam drive shaft 130 to rotate a cam plate 132 upon which there is an upstanding drive pin 134 and support 136. The cam plate 132 rotates about the axis 138.

As the cam plate 132 rotates about the axis 138, the drive pin 134 periodically engages slots 140 in a cam wheel 142, to rotate the cam wheel 142 in the direction indicated by the arrow 144 for rotation of the cam plate 138 in the direction indicated by the arrow 146. While the drive pin 134 is in driving engagement with one of the slots 140, the rotation of the cam plate 142 rotates the first drive shaft 62 about the first axis 66, thereby rotating the first pulley 64 to move the first drive belt 72. When the drive pin 134 is free of the slots 140, as illustrated in FIGS. 6 and 7, the support member 136 engages the lobes 148 of the cam wheel 142 to provide support therefor to prevent rotation of the cam wheel 142. Thus, the Geneva drive 124 provides periodic and sequential movement of the first drive belt 72, followed by periodic and sequential dwell times, where there is no rotation of the first drive shaft 62 and therefore no movement of the first drive belt 72. Such movement allows the sequential positioning of the plurality of cup-like sample wells 54 in the tray 52 to be positioned in alignment with the aperture defined by the walls 48.

For illustrative purposes, the second drive means 60 comprises a stepping motor 150 to rotate the second drive shaft 84 about the third axis 86. The stepping motor 150 is of conventional design. It will be appreciated, however, that a Geneva drive may be utilized for both the first drive means 58 and the second drive means 60. Alternatively, stepping motors, such as stepping motor 150 may be utilized for both the first drive means 58 and the second drive means 60. In other applications, other forms of drive may be provided, as desired.

Figure 8:
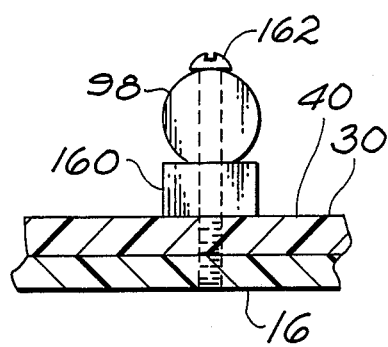
FIG. 8 is a partial sectional view along the line 8—8 of FIG. 3.

FIG. 8 is a view along the line 8—8 of FIG. 3, and illustrates the mounting arrangements for the first second, and third guide rod means 74, 96, and 98, respectively, of the motion producing means 56. Thus, while the third guide rod 98 is illustrated in FIG. 8, the mounting of each of the first, second, and third guide rods is similar, with such a structure of each end thereof. The guide rod 98 is mounted on a block 160, coupled to the lower surface 40 of the top wall portion 16, and a screw means 162 extends through the guide rod 98, through the block 60, and threadingly engages the mounting plate 30, and, if desired, the top well portion 16.

Figure 9:
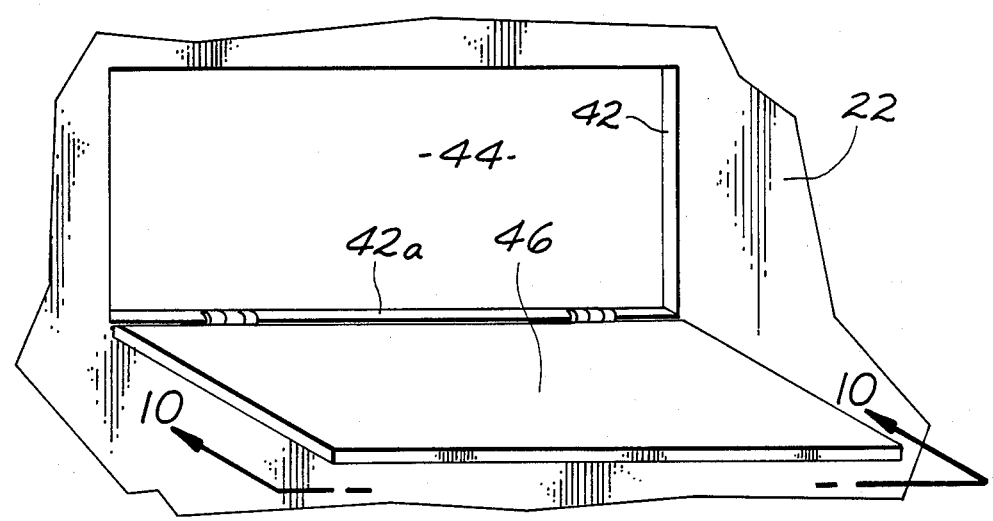
FIG. 9 is a partial perspective view of a portion of the embodiment shown in FIG. 1.

FIG. 9 illustrates a partial view, in perspective, of the tray receiving aperture 44, with the door 46 in the front wall 22 in the open position. The tray holder means 50 has been omitted for clarity therein.

FIG. 10 illustrates the tray holder means 50 according to the principles of the present invention. As shown in FIG. 10, the tray holder means 50 comprises a generally box-like structure having a mask plate 170, having a plurality of walls 172 defining a plurality of apertures 174 therethrough. The number of the plurality of apertures in the mask plate 170 corresponds to the number of cup-like sample wells 54 contained in the tray 52, and are aligned therewith. The tray holder means also has opposed side walls 174 and 176 and a bottom plate 178. The bottom plate 178 has walls 180, defining an aperture therethrough, to allow insertion of a tray support 182 therethrough. The tray support 182 is mounted on a pair of spindles 184 and 186, which extend through a plate 180, coupled to the bottom plate 178. A pair of guide bushings 192 and 194 provide guidance for the spindles 184 and 186. A transverse plate 196 couples the remote ends of the spindles 184 and 186. A crank means, generally designated 198 is mounted on the plate 190, and coupled to the plate 196, and is an overcentered type crank means for raising and lowering the plate 182 by movement of the crank means handle 200 in the directions indicated by the double ended arrow 202. In the up position thereof, the plate 196 is positioned adjacent the bushings 192 and 194 and the cup-like sample walls 54 are closely adjacent the mask plate 170 and in alignment with the apertures 174 therein. The tray 52 may be loaded and unloaded from the tray holder means 50 when the tray holder means 50 is in a load position, and extending through the aperture 44 defined by the edges 42 and the door 46 in the open position thereof.

In order to detect and measure the luminescence emitted from each of the cup-like sample wells 54, a luminescence detection means 220 is provided in upper chamber 34 mounted on the upper surface 38 of the top wall portion 16, in regions adjacent the aperture defined by the walls 48. FIG. 11 is a partial sectional view, partially in schematic form, of the luminescence detection means 220. As shown on FIG. 11, the luminescence detection means 220 comprises a plug means 222, which, for example, may be a force fit into the aperture defined by the walls 48 and the plug means 222 has walls 224 defining a lens aperture 226 therethrough in which a lens 228 is positioned. The lens aperture 226 preferably has a narrowed portion 230 at the inlet thereto in the base chamber 28, and a cross sectional area of the narrowed portion 230 is preferably somewhat smaller than the cross sectional area of the cup-like sample wells 54. Luminescence emitted from each of the cup-like sample wells 54 is directed through the entrance portion 230 of the lens aperture 226 and passes through the lens 228 as indicated by the arrows 232 and strikes a prism 234, which redirects the luminescence as indicated by the arrows 236 into a photo-multiplier tube 238. The photo-multiplier tube 238 generates a signal having a magnitude proportional to the intensity of the luminescence emitted from each of the cup-like sample wells 54. A substantially lightproof case means 240 surrounds the photo-multiplier tube 238 and prism 234 and the plug means 222 extends through the luminescence detector case 240, an illustrated in FIG. 11.

In many applications, it is desired to add certain reagents to each of the cup-like sample wells 54 in order to cause the luminescence immediately prior to the positioning of the well in alignment with the plug means 222. Thus, the cup-like sample well 54a in FIG. 11 is emitting luminescence and the intensity thereof is being detected by the photo-multiplier tube 238. During such measurement, the tray holder means 50 is stationary in the position illustrated in FIG. 11. The next cup-like sample well 54b is the one which will be measured next for movement of the tray holder means in the direction indicated by the arrow 80a. When the cup-like sample well 54b is in the position as shown in FIG. 11, reagents may be added thereto from a fluid dispensing means generally designated 250 and shown in schematic diagram form. The reagent is automatically injected in a predetermined amount, through the dispensing tube 252, when the cup-like sample well 54b is in the position shown. Structures for sequentially dispensing one or more fluids in a periodic time sequence are well known and any of such devices may be utilized in connection with the invention herein. If the tray holder means 50 is moving in the direction indicated by the arrow 80b, then the cup-like sample well 54c would be the next one whose luminescence is to be measured, and, consequently, the fluid dispensing means 250 dispenses the fluids at the position of cup-like sample well 54c illustrated in FIG. 11, as shown by the dotted line showing of the dispensing tube 252.

In the operation of the invention of the embodiment 10, the second drive means, such as the stepping motor 150, sequentially moves the tray holder means 50 so that each of the eight rows of cup-like sample wells are sequentially aligned with the aperture defined by the walls 48. In each of such positions defined by the second drive means, the first drive means indexes the tray holder means 50 to each of the twelve column positions so that each cup-like sample well 54 is sequentially positioned for the luminescence emitted therefrom to be detected by the photo-multiplier tube 238.

As illustrated in FIG. 3, position detection means 260, 262, and 264 are provided to indicate the position of the tray holder means 50. For example, one position to be indicated may be that occurring when the tray holder means 50 is in the load position thereof, as described above. To achieve a signal indicative of the load position, the position indicating means 260 and 264 are utilized. FIG. 12 is the view along the line 12—12 of FIG.

3, and illustrates the position indicating means 260 and, it will be appreciated, the position indicating means 264 operates in the same way to generate a position signal indicative of the load position of the tray holder means 50. As shown on FIG. 12, the position indicating means 250 has a photocell, generally designated 270, in which light is constantly emitted between the portions 272 and 274 thereof. An opaque tab means 276 is positioned between the portions 272 and 274 when the tray holder means is in the load position for movement in the direction indicated by the arrow 80. Similarly, a tab means 280 is mounted on the second slide means 102 and performs the same function with third position indicator 264 to indicate the load position for movement in the direction indicated by the arrow 110. In order to determine which row is in a position to be aligned with the lens aperture 226, a rate-like position indicator 298, having alternate opaque portions 292 and transparent portions 294 is coupled to the second slide means 102 to engage the third position indicator 262 which generates the position signals desired. The third position indicator 262 is based at a different level from the lower surface 40 of the top wall portions 16 than the second position indicator 264, so that there is no interference therebetween, or with the tab means 208.

In order to calibrate or in determining the functional status of the present invention, it is preferred that a calibration light source be provided which may be selectively energized to check the operational condition of the embodiment 10. FIG. 13 illustrates the structure associated with such a calibration light source, generally designated 300, which is coupled to the bottom wall 26 in alignment with the plug means 222. In FIG. 13, the structure associated with the tray holder 50 and motion producing means 56 in the base chamber 28, has been omitted for clarity. The calibration light source 30 has a source of light of, preferably, known intensity as indicated at 302, which is selectively energized prior to the testing operation of the present invention. Light is emitted therefrom and passes through the same optical system described above for the detection of luminescence and into the photo-multiplier tube in order that operation thereof may be checked and/or calibrated for particular applications.

Figure 14:
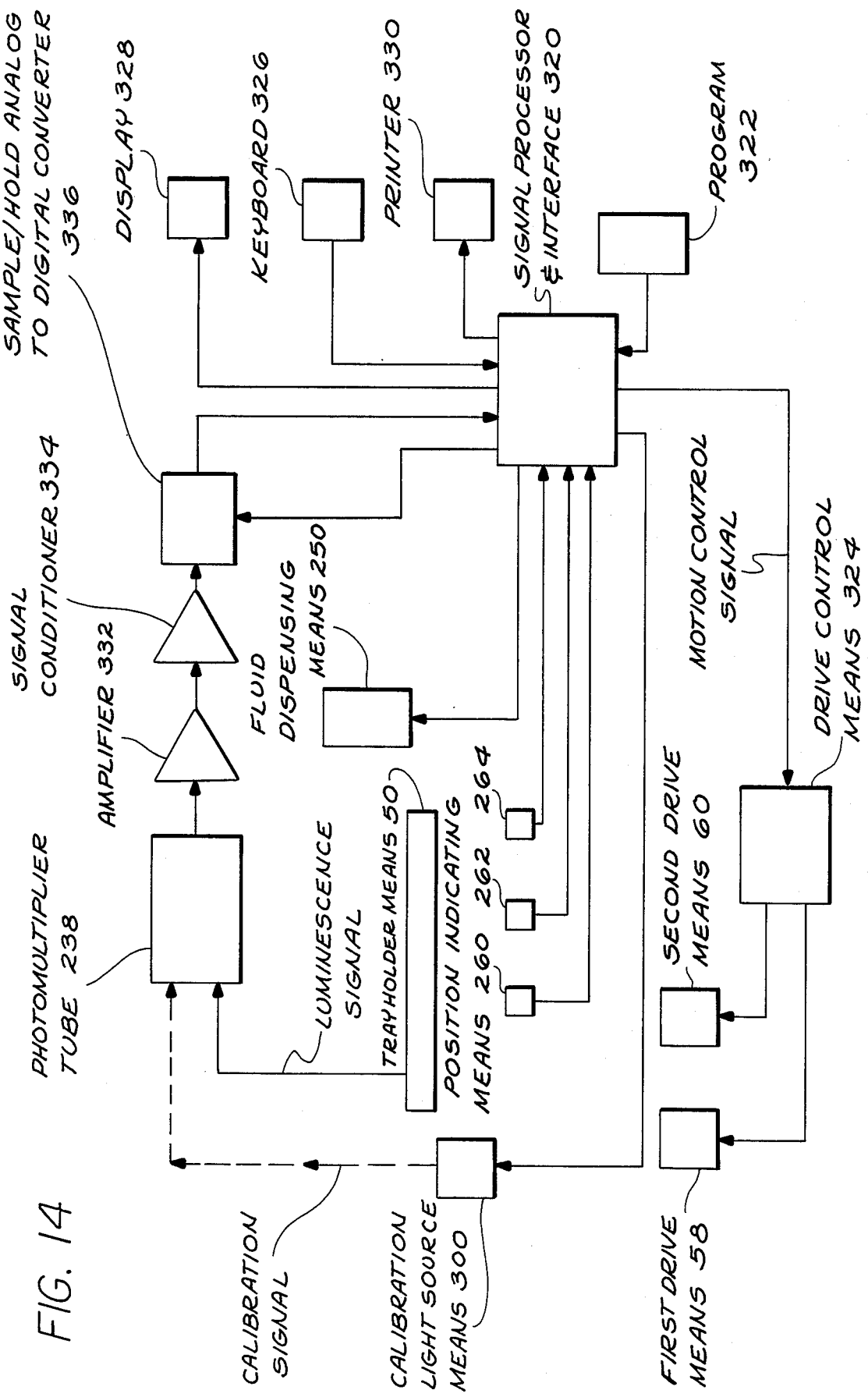
FIG. 14 is a functional block diagram, illustrating the operational controls of the present invention.

FIG. 14 is a functional block diagram of the structure, controls, and signals utilized in the practice of the present invention. As shown on FIG. 14, a signal processor and interface 320 receives the various signals generated by the different portions of the present invention and provides the various signals for controlling the operation of the present invention. A program 322 generates the control sequence for the signal processor 320. The program 322 can, of course, define any desired set of sequential operations required for particular applications of the present invention. The signal processor and interface 320 generates a motion control signal which is applied to the drive control means 324, which generates the individual drive control signals applied to the first drive means 58 and second drive means 60 for controlling the movement of the tray holder means 50. The position indicating measns 260, 262, and 264 generate the respective position control signals which are applied to the signal processor 320. The signal processor 320 also generates the applicable control signal which is applied to the fluid dispensing means 250 when such fluid dispensing means is utilized for controlling the dispensing of one or more fluids into the cup-like sample walls as required in particular applications. A keyboard 326 (illustrated pictorially on FIG. 1) is also provided for manual input of desired control signals to the signal processor 320, so that preselected operations such as movement of the tray holder means 50, dispensing of fluids from the fluid dispensing means 250, operation of the calibration light source means 300, or the like, may be done manually, independent of the status of the program 322.

A visual display, such as an LED display 328, may be provided, and is also illustrated pictorially on FIG. 1. The display 328 provides a visual indication of any desired function or process indicative of the state of the various functions of the invention. A printer 330 is also provided and illustrated pictorially on FIG. 1, for providing a digitalized printout of, for example, the signals generated by the photo-multiplier tube 238.

The photo-multiplier tube 238 receives the luminescence signal emitted from the cup-like sample wells and generates an output signal, having a magnitude proportional to the intensity of the luminescence signal. The photo-multiplier output signal is applied to an amplifier 332 and the amplified signal is applied to a signal conditioner 234. The signal conditioner may be of any desired type, depending upon the particular application and the particular types of displays required in such an application. For example, where a digitalized output record is provided by the printer 330, the output from the signal conditioner is fed into a sample/hold analog to digital converter 336 to convert the output signal from the signal conditioner 334 from an analog to a digital signal which is then applied to the signal processor 320 and the printer 330 prints the corresponding digitalized signal for each luminescence detected. The signal conditioner 334 may, if desired, include a means for deriving an analog signal having a magnitude proportional to the square root of the magnitude of the signal from the amplifier 332. In some applications, this is desired to expand the magnitude of the signal from comparatively low intensity luminescence signals and correspondingly compress the magnitude for high intensity luminescence signals. Suitable controls, if desired, may be included in the analog to digital converter 326 to square the signals obtained, and thereby put such signals into a linear relationship.

This concludes the description of the present invention. From the above, it can be seen that there has been provided an improved luminescence detection and measurement arrangment which provides for the rapid and accurate measurements of the luminescence emitted from a plurality of luminescence emitting samples. Those skilled in the art may find many variations and adaptations of the present invention and all such variations and adaptations, falling within the true scope and spirit of the appended claims, are intended to be covered thereby.

What is claimed is:

1. A luminescence measurement arrangement comprising, in combination:
   a case means, having first walls comprising a top wall portion, opposed side wall portions, a front wall portion, and a back wall portion, said first walls defining a base chamber, and second walls defining an upper chamber, said upper chamber separated from said base chamber by said top wall portion of said first walls;
   said top wall portion of said first walls having an upper surface in said upper chamber, and a lower surface in said base chamber, and said top wall portion having edge walls defining an aperture therethrough, providing communication between said base chamber and said upper chamber;

said front wall portion of said first walls having edges defining a tray holder receiving aperture therethrough, providing communication between said base chamber and regions external thereof;

tray holder means movably mounted in said base chamber and having a load position extending through said tray receiving aperture in regions external said base chamber and movable to a plurality of internal positions in said base chamber, said tray holder means for receiving a tray having a plurality of cup-like sample wells in a predetermined spaced array;

motion producing means mounted on said top wall portion and operatively connected to said tray holder means for selectively moving said tray holder means between said load position to said plurality of internal positions, whereby a plurality of cup-like sample wells is positioned in a predetermined sequence in an aligned condition with said aperture in said top wall portion;

luminescence detection means mounted on said top wall portion in said upper chamber for detecting the luminescence emitted from one of a plurality of cup-like sample wells in an aligned condition with said aperture in said top wall portion for said tray holder means in each of said plurality of internal positions thereof, and generating an output signal having a magnitude proportional to the intensity of the detected luminescence;

display means for receiving said output signal from said luminescence detection means and providing a detectible display proportional to said output signal in regions external said case means.

2. The arrangement defined in claim 1, wherein: said base chamber is substantially free of light emanating from regions external thereof, for the condition of said tray holder means in said plurality of internal positions thereof.

3. The arrangement defined in claim 2, wherein: said motion producing means further comprises drive means for moving said tray holder means in mutually perpendicular directions in said base chamber.

4. The arrangement defined in claim 3, wherein: said drive means further comprises a first drive means for moving said tray holder in first directions of said mutually perpendicular directions, and a second drive means for moving said tray holder means in second directions of said mutually perpendicular directions.

5. The arrangement defined in claim 4, wherein: at least one of said first drive means and said second drive means comprises a Geneva drive means.

6. The arrangement defined in claim 4, wherein: said first drive means and said second drive means further comprise load position indicating means for detecting said tray holder means in said load position thereof, and generating first position signals in response thereto.

7. The arrangement defined in claim 6, wherein: at least one of said first and second drive means further comprises internal position detection means for detecting a preselected number of said plurality of internal positions of said tray holder means and generating second position signals in response thereto.

8. The arrangement defined in claim 4, wherein: said first drive means further comprises:

a first Geneva drive means mounted on said upper surface of said top wall portion in said upper chamber, and having a rotatable first drive shaft means extending through said top wall portion into said base chamber;

a first pulley and a second pulley rotatably mounted on said lower surface of said top wall portion in said base chamber, and in spaced apart relationship, for rotation about a first axis and second axis, respectively, said first pulley mounted on said first drive shaft for rotation therewith;

first belt means around said first pulley and said second pulley, and movable therearound for the condition of rotation of said first pulley;

first guide rod means mounted on, and spaced from, said lower surface of said top wall portion in said base chamber, and aligned substantially parallel to the plane containing said first axis and said second axis;

first slide means, slidably mounted on said first guide rod means and coupled to said first belt means for movement therewith between said first pulley and said second pulley, in said first directions of said mutually perpendicular directions; and said tray holder means operatively connected to said first slide means for movement therewith.

9. The arrangement defined in claim 8, wherein: said second drive means further comprises:

a second rotatable drive shaft, extending through said top wall portion from said upper chamber to said base chamber;

a third pulley and a fourth pulley, rotatably mounted on said lower surface of said top wall portion in said beam chamber for rotation about a third axis and a fourth axis, respectively, and said third axis and said fourth axis in a plane substantially perpendicular to the plane containing said first axis and said second axis, and said third pulley mounted on said second drive shaft for rotation therewith;

second belt means around said third pulley and said fourth pulley for motion therearound for the condition of rotation of said third pulley;

second guide rod means and third guide rod means mounted on and spaced from said lower surface of said top wall portion in said base chamber in parallel, aligned, spaced apart relationship and parallel to the plane containing said third axis and said fourth axis;

second slide means, slidably mounted on said second guide rod means and coupled to said second belt means for movement therewith, between said third pulley and said fourth pulley, said second directions of said mutually perpendicular directions; and said tray holder means operatively connected to said second slide means for movement therewith.

10. The arrangement defined in claim 9, wherein: said motion producing means further comprises:

third slide means, slidingly mounted on said third guide rod means for sliding movement therealong;

fourth guide rod means coupled to said second slide means and said third slide means, and extending therebetween, and said fourth guide rod means substantially parallel to said first guide rod means for movement with said second and third slide means;

fourth slide means, coupled to said tray holder means and slidingly mounted on said fourth guide rod means for movement therewith;
fifth guide rod means, coupled to said first slide means and extending therefrom in a direction substantially parallel to said third guide rod means and said fourth guide rod means; and
fifth slide means, coupled to said tray holder means and slidably mounted on said fifth guide rod means for movement therealong.

11. The arrangement defined in claim 10, wherein said second drive means further comprises:
a stepping motor means mounted on said upper surface of said top wall portion in said upper chamber for rotating said second drive shaft.

12. The arrangement defined in claim 10, wherein said second drive means further comprises:
a second Geneva drive means, mounted on said upper surface of said top wall portion for rotating said second drive shaft.

13. The arrangement defined in claim 10, wherein:
said fourth slide measns, comprises two spaced apart slide bearing means; and
said fifth slide means, comprises two spaced apart slide bearing means.

14. The arrangement defined in claim 10, wherein:
said motion producing means further comprises drive control means for selectively energizing said first drive means and said second drive means to selectively rotate said first drive shaft and said second drive shaft, whereby said tray holder means is selectively moved in said mutually perpendicular direction.

15. The arrangement defined in claim 4, wherein:
said luminescence detection means further comprises a photo-multiplier tube.

16. The arrangement defined in claim 15, wherein:
said luminescence detection means further comprises:
plug means having walls defining a lens aperture therethrough mounted in said aperture in said top wall portion and having a lens means therein for transmitting said luminescence from the cup-like sample well in aligned relationship to said lens aperture into said upper chamber;
prism means for receiving said luminescence from said lens means and directing said luminescence to said photo-multiplier tube; and
light shield means for shielding said photo-multiplier tube from ambient light external said light shield means.

17. The arrangement defined in claim 16, wherein:
said lens aperture in said plug means has a smaller cross section area than each of the cross section areas of the open end of the cup-like sample wells; and
one of said plurality of said cup-like sample wells aligned with said lens aperture at each of said internal positions of said tray holder means; and
said tray holder means further comprises:
mask means mounted thereon and having a wall defining a plurality of mask apertures therethrough, said plurality of mask apertures corresponding to the number of the plurality of cup-like sample wells in the tray, and one of said apertures aligned with each of the cup-like sample wells and having a cross sectional diameter substantially corresponding to the cross sectional area of the cup-like sample wells.

18. The arrangement defined in claim 17, wherein:
said tray holder means further comprises:
tray support means movable from a load position to a detection position for positioning a tray of cup-like sample wells closely adjacent said mask means for tray holder means in the plurality of internal positions thereof.

19. The arrangement defined in claim 17, and further comprising:
calibration light source means, mounted in said base chamber for selectively emitting a predetermined intensity of light through said lens aperture.

20. The arrangement defined in claim 17, wherein:
said tray holder means further comprises:
alignment means for aligning the tray of cup-like sample wells in a predetermined position therein, for alignment with said mask means.

21. The arrangement defined in claim 8, wherein:
said motion producing means further comprises:
sequencing means for receiving said first position signals and said second position signals and selectively controlling said first drive means and said second drive means in response thereto.

22. The arrangement defined in claim 1, wherein:
said display means further comprises:
printer means for sequentially providing a digitalized printed display, corresponding to the intensity of luminescence detected from each cup-like sample well.

23. The arrangement defined in claim 1, and further comprising:
fluid dispensing means, operatively connected to said case means for selectively dispensing predetermined fluids in a predetermined timed sequence into each cup-like sample well.

24. The arrangement defined in claim 23, wherein:
said fluid dispensing means further comprises:
control means for selectively and sequentially dispensing more than one fluid into each cup-like sample well.

25. The arrangement defined in claim 23, wherein:
said fluid dispensing means dispenses fluid into a cup-like sample well before such cup-like sample well is in an aligned condition with said aperture in said top wall portion of said first walls.

26. A luminescence measurement arranged comprising, in combination:
a case means, having walls defining a cavity;
tray holder means movably mounted to said case means and having a load position extending external said case means and movable to a plurality of internal positions in said case means, said tray holder means for receiving a tray having a plurality of cup-like sample wells in a predetermined spaced array;
motion producing means mounted on said case means and operatively connected to said tray holder means for selectively moving said tray holder means between said load position to said plurality of internal positions, whereby a plurality of cup-like sample wells are positioned in a predetermined sequence in predetermined positions in said case means;
luminescence detection means mounted on said case means in luminescence receiving relationship to the plurality of cup-like sample wells for detecting the luminescence emitted from one of a plurality of cup-like sample wells in each of said plurality of internal positions thereof, and generating an output signal having a magnitude proportional to the intensity of the detected luminescence;

display means for receiving said output signal from said luminescence detection means and providing a detectible display proportional to said output signal in regions external said case means.

* * * * *